(12) United States Patent
Young (10) Patent No.: US 7,887,516 B2
(45) Date of Patent: Feb. 15, 2011

(54) SAFETY CAP FOR MEDICAL NEEDLES (75) Inventor: Christopher S. Young, South Kent, CT (US)

(73) Assignee: ISPG, Inc., New Milford, CT (US)

( * ) Notice: Subject to any disclaimer, the term of this patent is extended or adjusted under 35 U.S.C. 154(b) by 1344 days.

(21) Appl. No.: 11/402,752

(22) Filed: Apr. 12, 2006

(65) Prior Publication Data

US 2007/0255211 A1 Nov. 1, 2007

(51) Int. Cl.
*A61M 5/32* (2006.01)

(52) U.S. Cl. ...................................... 604/192

(58) Field of Classification Search ................. 604/110, 604/192
See application file for complete search history.

(56) References Cited

U.S. PATENT DOCUMENTS

| | | | | |
|---|---|---|---|---|
| 4,161,943 A * | 7/1979 | Nogier | ......................... | 600/12 |
| 4,380,292 A * | 4/1983 | Cramer | ....................... | 206/366 |
| 4,883,470 A * | 11/1989 | Haindl | ....................... | 604/192 |
| 5,242,421 A * | 9/1993 | Chan | ........................... | 604/198 |
| 5,419,766 A * | 5/1995 | Chang et al. | ................. | 604/110 |
| 5,527,283 A * | 6/1996 | Swisher, III | ................. | 604/110 |
| 5,718,689 A * | 2/1998 | Stevenson | .................... | 604/192 |
| 5,758,650 A * | 6/1998 | Miller et al. | ................. | 600/461 |
| 5,997,513 A * | 12/1999 | Smith et al. | .................. | 604/198 |
| 6,511,461 B2 * | 1/2003 | Jonsson | ....................... | 604/240 |
| 2005/0192535 A1* | 9/2005 | Takagi et al. | ........... | 604/164.08 |
| 2007/0088260 A1* | 4/2007 | Peng | ........................... | 604/110 |

* cited by examiner

*Primary Examiner*—Nicholas D Lucchesi
*Assistant Examiner*—Aarti B Berdichevsky
(74) *Attorney, Agent, or Firm*—Alix, Yale & Ristas, LLP (57) ABSTRACT

To protect against the health and safety risks that accompany accidental post-use needle sticks, a medical needle assembly equipped with a safety cap is described. The disclosed medical needle assembly generally includes a needle hub, a needle having a magnetized distal end, and a removable safety cap attached to and extending radially from the needle hub. In another embodiment, the removable safety cap is attached to a sheath that covers the needle. The safety cap includes a magnet and a retainer disposed between the first and second ends of the cap. The retainer is configured to prevent withdrawal of the needle once the needle perforates the retainer and the safety cap encloses the distal end of the needle.

20 Claims, 7 Drawing Sheets

SAFETY CAP FOR MEDICAL NEEDLES

FIELD OF THE INVENTION

This invention relates generally to medical needles, and more particularly, to needle and introducer assemblies that include a post-use protective cap for the needle tip.

BACKGROUND OF THE INVENTION

The safety and health risks associated with inadvertent needle sticks has long been recognized, particularly when the needles have come into contact with bodily fluids contaminated with an infectious disease such as HIV or Hepatitis. In light of the high risk of injury and possible transmission of disease, it is critical that individuals be protected from inadvertent contact with the needle tip after the needle has been used. Generally, needle and catheter introducer assemblies are intended as single-use devices and are disposed of after use. However, it is often difficult to properly dispose of a used needle while caring for a patient, especially under the stress of medical emergencies.

Procedures for removing a needle from a patient commonly require a technician to use one hand to place pressure at the injection site where the needle is being withdrawn, while removing the needle device with the other hand. It is also common for medical personnel to give higher priority to caring for the patient than to the disposal of a needle. Typically, disposing of medical needle devices without safety shields or caps requires a sharps container to be within reach so that attending medical personnel do not have to leave the patient's side. However, the events and/or distractions surrounding a particular treatment situation can result in needles not being immediately and properly disposed of after use or erroneously identified as being uncontaminated.

Consequently, under many medical treatment situations the chances for injury and/or infection due to an accidental needle stick or re-use of a contaminated needle is dangerously high. As such, a medical needle assembly that reduces the health and safety risks associated with improper handling and disposal of used and contaminated medical needles is needed.

The present invention addresses this need by providing a medical needle assembly that can be capped immediately after use, even under the stress of a medical emergency, in a quick, convenient and tamper-resistant manner.

SUMMARY OF THE INVENTION

To protect against the health and safety risks that accompany accidental post-use needle sticks, the present invention provides a medical needle assembly equipped with a safety cap. The disclosed medical needle assembly generally includes a needle hub, a needle having a magnetized distal end, and a removable safety cap attached to and extending radially from the needle hub. The safety cap has an outer housing, a first end, a closed second end, and an interior cavity. The safety cap further includes a magnet disposed in the housing and a retainer disposed between the first and second ends of the cap. The retainer is configured to resist withdrawal of the needle once the needle is introduced into the cavity. Needle sticks are prevented when the needle perforates the retainer and the safety cap encloses the distal end of the needle.

BRIEF DESCRIPTION OF THE DRAWINGS

FIGS. 5A-D illustrate the method of capping a medical needle assembly according to the present invention;

DETAILED DESCRIPTION OF THE PREFERRED EMBODIMENTS

With reference to the drawings, wherein like numerals represent like elements throughout the various views, a medical needle assembly in accordance with the present invention is generally designated by the numeral 10. The needle assembly 10 employs a protective safety cap that is adapted for effective and efficient capping of the needle tip after usage.

Figure 1:
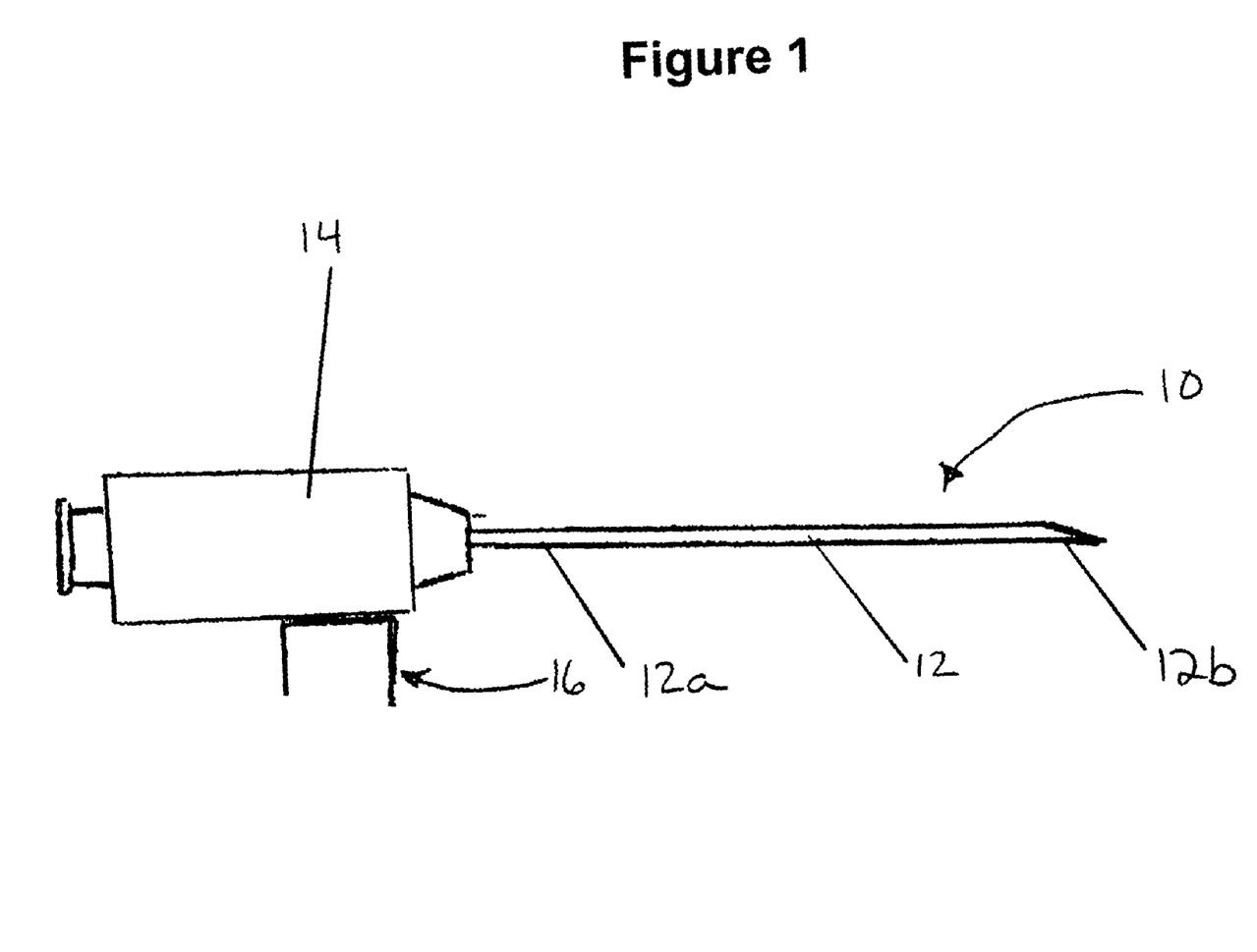
FIG. 1 is a side view of one embodiment of a medical needle assembly, including a removably attached safety cap, of the present invention.

An exemplary embodiment of the present invention is a specialty, large bore medical needle assembly 10 used in epidural and/or spinal anesthesia, such as Quincke and/or Tuohy needles. It should be understood, however, that the invention is not limited to specialty or large bore medical needles but rather extends to all medical needles. As illustrated in FIG. 1, the medical needle assembly 10 includes a needle 12 having a proximal end 12a and a distal tip end 12b. A needle hub 14 is attached to the proximal end 12a of the needle. The hub 14 may be of any conventional design used in standard medical practice, such as a hub having a luer lock for the attachment of syringes or other medical devices that require the attachment of a needle.

Figure 3A:
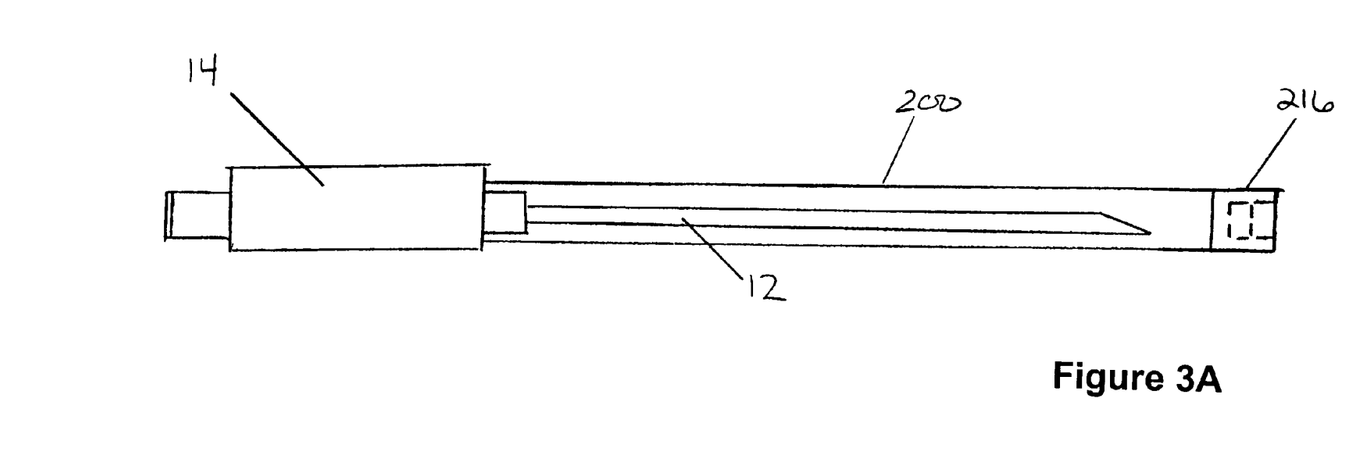
FIGS. 3A and 3B are side views of a second embodiment of a medical needle assembly, including a removably attached safety cap located on the needle sheath.
Figure 3B:
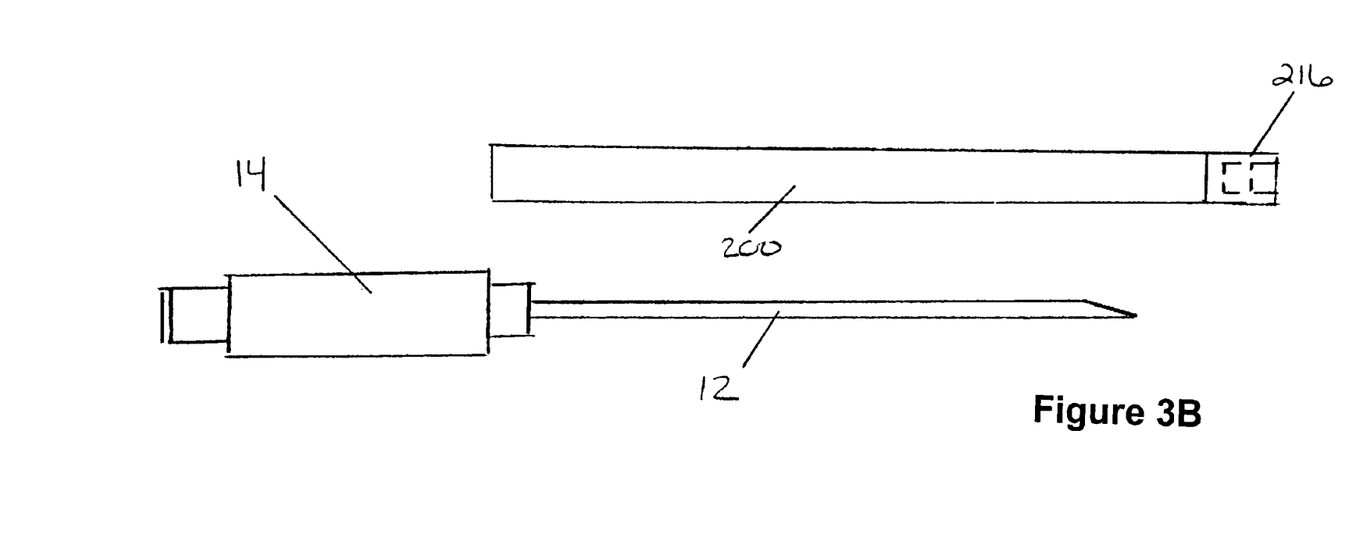

The hub 14 is further provided with at least one safety cap 16, which is easily removable. The safety cap 16 may be secured to the hub 14 in a variety of ways, such as a peg 18, which provides an interference fit, or a break-away tab. In the attached condition, the cap 16 projects radially from the hub 14 and can be quickly located and efficiently removed without the user having to look down at the assembly 10. In another embodiment, illustrated in FIGS. 3A and 3B, the medical needle assembly includes a sheath 200 over the needle 12. In the attached condition, the safety cap 216 is secured to or is part of the sheath 200, which is removed before use of the needle 12. The safety cap 216 can be detached from the sheath 200 when needed.

In a preferred embodiment, the distal tip end 12b of the needle is magnetized. Magnetization of the distal tip end of the needle is achieved during the fabrication process. Specifically, the distal tip end 12b is magnetized by introduction into a magnetic field produced by high-energy coils.

Figure 4A:
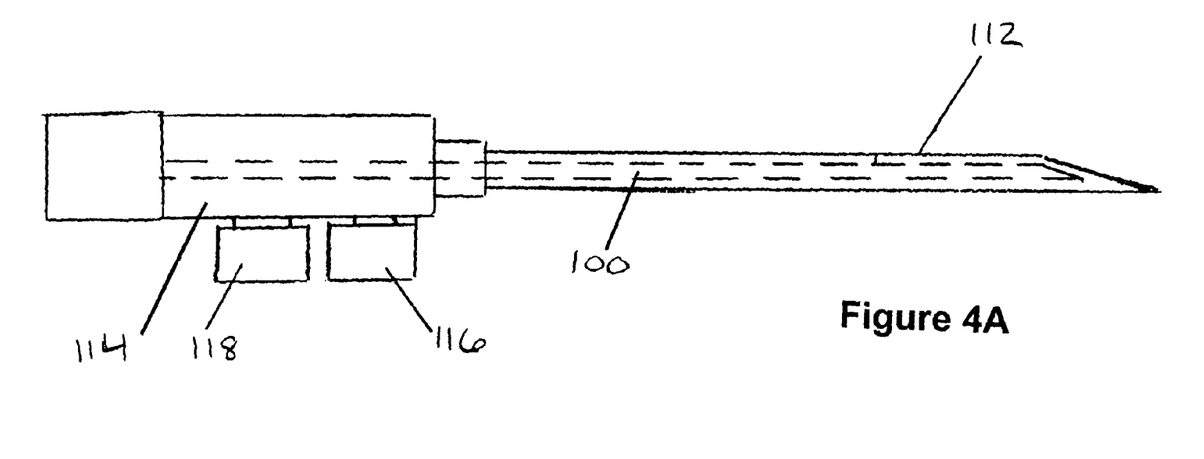
FIGS. 4A and 4B are side views, partly in schematic, of a third embodiment of a medical needle assembly, including multiple safety caps, of the present invention.
Figure 4B:
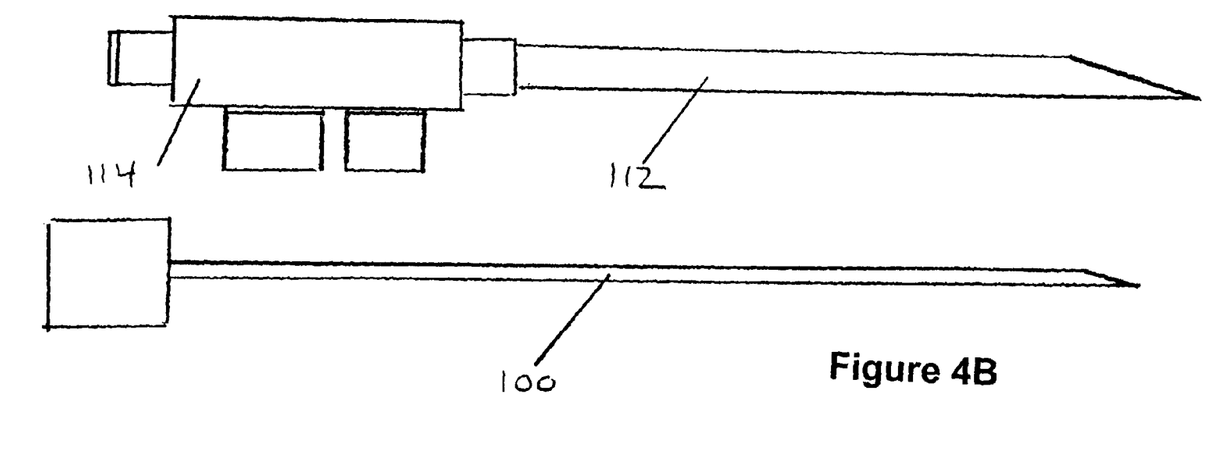

A third embodiment of the invention, as depicted in FIGS. 4A and 4B, is directed to needle assemblies having a stylet 100 within the needle or cannula 112 and multiple safety caps 116 and 118. According to this second embodiment, the hub 114 may be equipped with two safety caps 116 and 118, where a first cap 116 is used to cover the distal tip of a stylet 100 and a second cap 118 is used to cover the distal tip of the needle 112. In this second embodiment, both the needle 112 and stylet 100 may be magnetized.

Figure 2:
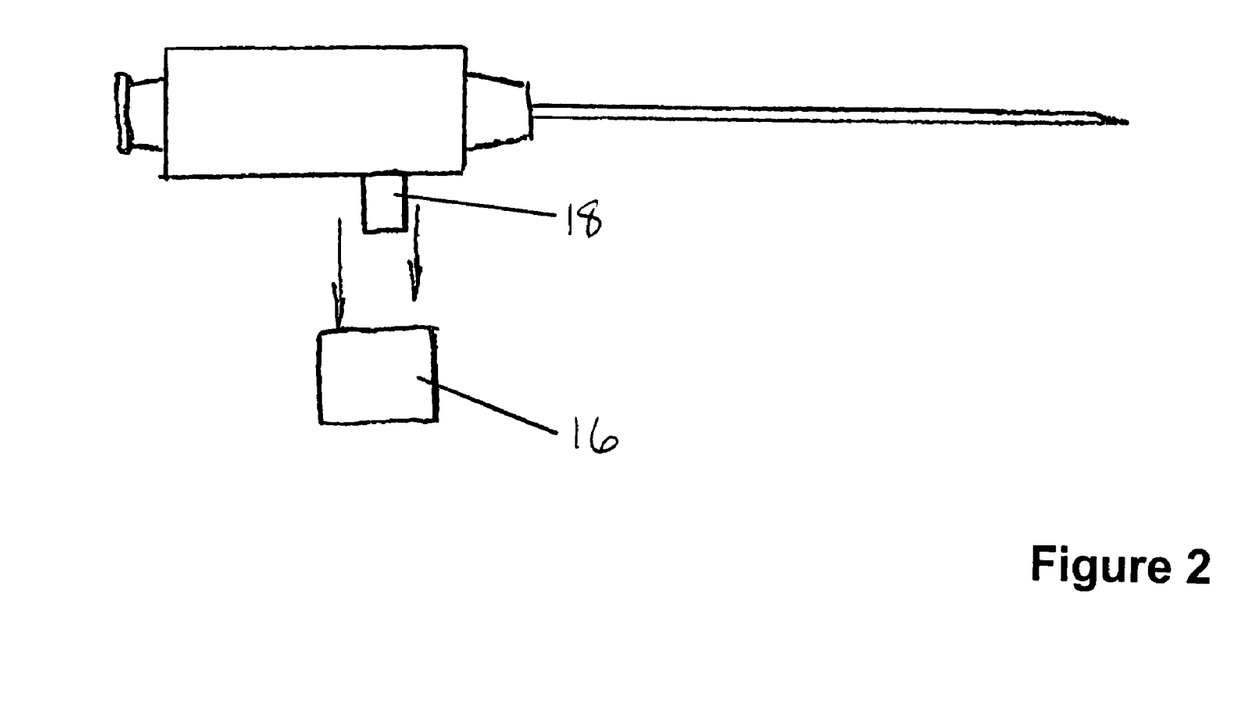
FIG. 2 is side view of the medical needle assembly of FIG. 1, wherein the safety cap is in the detached condition.

FIG. 2 depicts an embodiment of the safety cap 16 (or 116) in the detached condition. The means for securing the cap to the hub is designated generally as 18, and in the illustration takes the form of a peg.

Figures 6, 7:
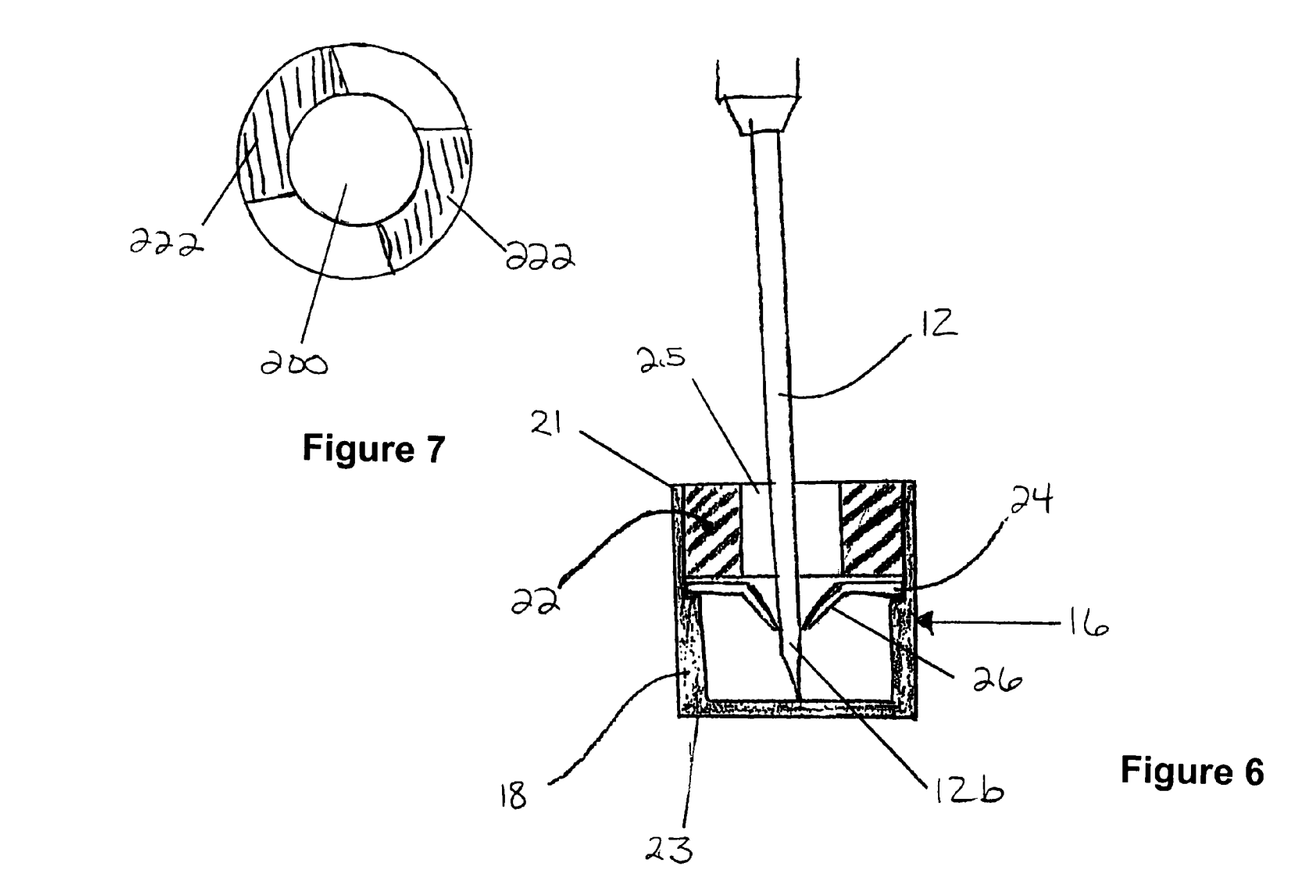
FIG. 6 is an enlarged fragmentary side view, partly in section, of the capped medical needle assembly of FIG. 5D.
FIG. 7 is another embodiment of a magnetic guide assembly for the present invention.

As best shown in FIG. 6, the safety cap is comprised of an outer housing 18, preferably plastic, a first open end 21, a second closed end 25, and a central cavity 25, which contains a magnetic guide 22. In one preferred embodiment, the magnetic guide 22 is an annular magnet that is coaxial with the central cavity 25 defined by the cap 16.

In another embodiment, the magnetic guide 222 is at least one arcuate magnet positioned adjacent to the central cavity 250. Preferably, there are two arcuate magnets (as shown in FIG. 7) or an annular magnet positioned adjacent to the central cavity.

Figures 8A, 8B, 8C:
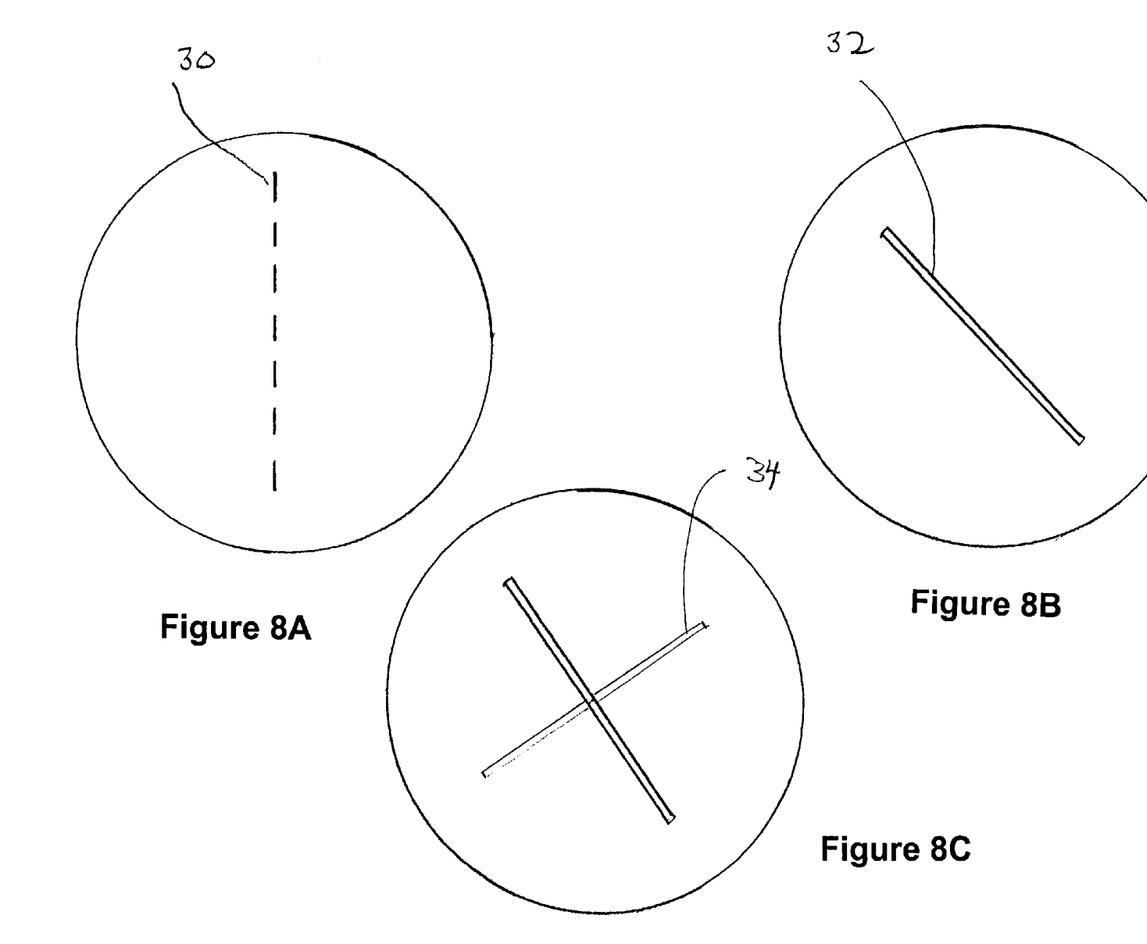
FIGS. 8A, 8B and 8C are enlarged top views of various embodiments of a retainer for the safety cap of FIG. 6.

A perforatable retainer 24 is disposed between ends 21 and 23. It is preferred that retainer 24 is a substantially planar disc manufactured from a resilient metal or plastic material that forms at least one resilient tab 26 when the distal tip 12b of the needle perforates the retainer 24. It should be understood that the described material of the retainer 24 does not limit the invention. The retainer 24 extends transversely of central cavity 25. The retainer 24 is either scored at 30 or has at least one slit 32 that extends across its center, as shown in FIGS. 8A and 8B respectively. In one preferred embodiment of FIG. 8C, the retainer 24 is scored in a "+" pattern 34. In another preferred embodiment, the retainer 24 has two slits that together form a "+" pattern.

The magnetized medical needle, the magnetic guide 22 (or 222), and the retainer 24 cooperate to provide for the efficient and effective protective capping of the needle tip after usage. The magnetization of the distal tip 12b aids the user by guiding the needle into the central cavity 25 of safety cap 16. The distal end 12b of the needle then perforates or pierces the retainer 24 to achieve the protected condition, i.e. where the safety cap 16 encloses the distal tip end 12b of the needle as seen in FIG. 5C.

When in the biased configuration, tab(s) 26 resist the withdrawal of the needle from the cap. Once the needle is in the protected condition, e.g. the tip is encased by the cap, the attractive forces between the magnetized distal tip 12b and the magnetic guide 22 help "lock on" the cap 16, thus providing additional protection against inadvertent re-exposure of the needle tip.

Figure 5A:
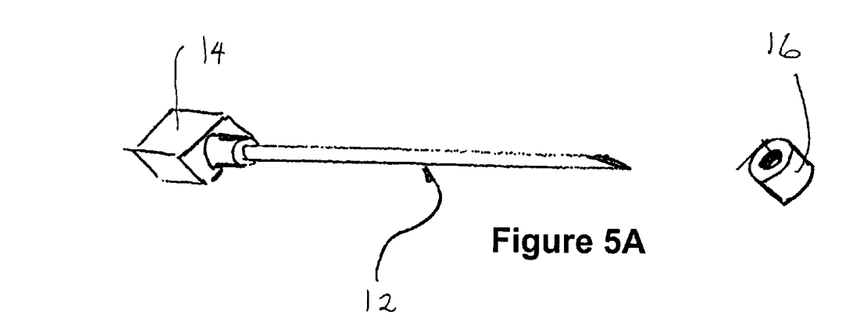
Figure 5B:
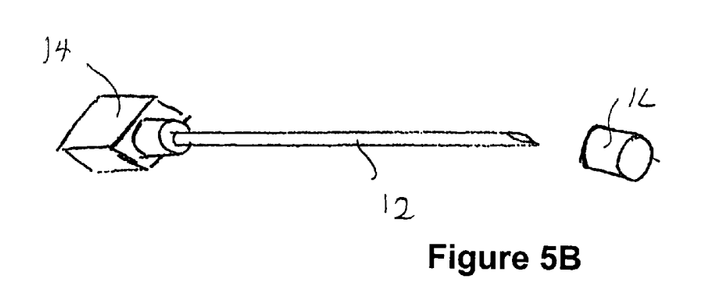
Figure 5C:
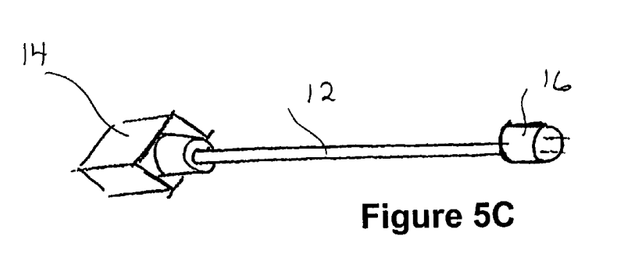
Figure 5D:
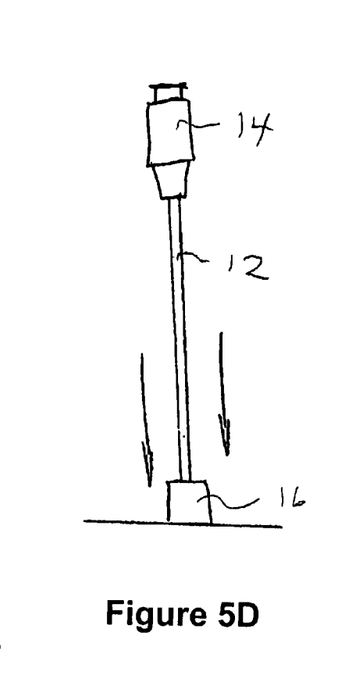

FIGS. 5A-5D illustrates the series of steps in utilizing the safety cap of the present invention so as to achieve the protected condition, i.e. where the safety cap 16 encloses the distal tip end 12b of the needle as seen in FIG. 5C. According to the invention, the needle is in the protected condition when the distal end 12b of the needle is advanced into the cap as shown in FIG. 5B, engages the retainer, and is prevented from subsequent removal or disengagement from the cap. As shown in FIG. 5D, in one preferred embodiment, the distal tip 12b of the needle engages and perforates the retainer by tamping the medical needle assembly on a surface. It should be understood that the present invention is not limited by the method of ensuring the engagement of the retainer.

When the distal tip 12b of the needle is advanced through the retainer 24, the retainer 24 forms at least one resilient tab 26. In a preferred embodiment, at least one tab 26 adopts a biased configuration by flexing towards the second end 23 of the safety cap 14, in the direction of needle movement. This biased configuration, shown in FIG. 6, functions to retain the cap on the needle.

Exemplary embodiments illustrating the medical needle assembly and the method of protecting users from post-use needle sticks are described for purposes of explanation and are not intended as limitations of the invention herein. Alternative designs and additional modifications may occur to one skilled in the art without departing from the spirit and the scope of the present invention.

What is claimed is:

1. A medical needle assembly, comprising:
   a needle having a proximal end and a magnetized distal end, and defining an axis extending from the proximal end to the distal end;
   a needle hub attached adjacent to said proximal end of said needle; and
   a safety cap attached to said needle hub and radially extending from said hub in a direction substantially perpendicular to said needle axis comprising:
   a housing having a first end and a closed second end and defining an interior cavity;
   a magnet disposed in said housing; and
   a retainer disposed between said first and second ends;
   wherein said cap is positionable on said distal end so that said distal end perforates said retainer and said cap encloses said distal end to create a protected condition such that the withdrawal of said distal end is resisted by a magnetic force between said distal end and said magnet and the engagement of the retainer against said distal end.

2. The medical needle assembly of claim 1, wherein said retainer comprises a substantially planar disc positioned perpendicular to the axis defined by said needle.

3. The medical needle assembly of claim 2, wherein said retainer is configured to form at least one resilient tab when said distal end perforates said retainer.

4. The medical needle assembly of claim 3, wherein at least one resilient tab flexes toward said second end as said distal end perforates said retainer.

5. The medical needle assembly of claim 4, wherein at least one resilient tab adopts a biased configuration that substantially prevents needle removal from said cap.

6. The medical needle assembly of claim 3, wherein said retainer is scored in a "+" shaped pattern across said axis.

7. The medical needle assembly of claim 3, wherein said retainer has at least one slit across said axis.

8. The medical needle assembly of claim 3, wherein said retainer has two slits in a "+" shaped pattern across said axis.

9. The medical needle assembly of claim 1, wherein said magnet is substantially annular and defines an opening that aligns with a central axis defined by the housing.

10. The medical needle assembly of claim 1, wherein said magnet is arcuate.

11. A medical needle assembly, comprising:
    a needle having a proximal end and a magnetized distal end, and defining an axis extending from the proximal end to the distal end;
    a needle hub attached to said proximal end of said needle and a safety cap radially extending from said hub in a direction substantially perpendicular to said needle axis comprising:

an outer plastic housing having a first end and a second end defining an interior cavity;

at least one guide adjacent said first end having an opening concentric with said axis; and a retainer adjacent said second end and defining a plane substantially perpendicular to the axis defined by the needle and adapted to flex between a biased position and an unbiased position.

12. The medical needle assembly of claim 11, wherein said guide is an arcuate magnet.

13. The medical needle assembly of claim 11, wherein said retainer adopts a biased configuration when said needle is advanced through the plane defined by said retainer.

14. The medical needle assembly of claim 13, wherein said biased configuration substantially prevents exposure of the distal end of said needle.

15. The medical needle assembly of claim 14, wherein said retainer is a disc of metal or plastic.

16. The medical needle assembly of claim 11, wherein said needle hub has a second radially extending cap.

17. The medical needle assembly of claim 16, further comprising a stylet removably inserted in said needle and having a magnetized tip end.

18. A method of capping a medical needle assembly comprising:

providing a medical needle defining an axis extending from a proximal end to a distal end with at least a magnetized distal end and a safety cap having a magnetic guide and a retainer removably attached to said medical needle, the safety cap radially extending from the needle in a direction substantially perpendicular to said needle axis;

detaching said safety cap from said medical needle;

guiding said distal end of said needle into said cap using attractive magnetic forces between said distal end and said magnetic guide; and engaging said retainer with said distal end to form a biased configuration and enclose said distal end such that withdrawal of said distal end is substantially prevented.

19. The method of claim 18, wherein the step of engaging said retainer further includes the steps of:

perforating said retainer;

forming at least one resilient tab; and tamping said medical needle assembly.

20. The method of claim 18, further comprising the step of flexing the retainer in the direction of needle movement.

\* \* \* \* \*